United States Patent [19]

Fugier et al.

[11] Patent Number: 4,652,692
[45] Date of Patent: Mar. 24, 1987

[54] NEW PROCESS FOR THE PREPARATION OF 1,3,5-UNDECATRIENES

[75] Inventors: Claude Fugier, Le Havre; Michel Leroux, Bolbec; Jean F. Normant, Bourg La Reine; Alexandre Alexakis, Paris, all of France

[73] Assignee: Oril S.A., Neuilly-sue-Seine, France

[21] Appl. No.: 863,124

[22] Filed: May 14, 1986

[30] Foreign Application Priority Data

May 31, 1985 [FR] France .................................. 85 08181

[51] Int. Cl.$^4$ .............................................. C07C 2/00
[52] U.S. Cl. ...................................................... 585/600
[58] Field of Search ........................................... 585/600

[56] References Cited

U.S. PATENT DOCUMENTS 3,532,762 10/1970 Corbier ............................... 585/600
4,014,951 3/1977 Naf et al. ............................. 585/600

FOREIGN PATENT DOCUMENTS 7407364 12/1974 Netherlands ........................ 585/600

OTHER PUBLICATIONS

Bloch et al., Tetrahedron Lett; vol. 26, 1301–04, (1985).
Mahajan et al., Indian J. Chem., vol. 11, 207–8, (1973).
Hayathi et al., Tetrahedron Lett, vol. 24, 2665–68, (1983).
Giraudi et al., Tetrahedron Lett., vol. 24, 489–492, (1983).
Nef et al., Tetrahedron Lett, vol. 23, 5043–46, (1982).
Nef et al., Helv. Chem, Acta., vol. 58, 1016–1037, (1975).

*Primary Examiner*—Asok Pal
*Attorney, Agent, or Firm*—Gordon W. Hueschen

[57] ABSTRACT

Process for the preparation of 1,3,5-undecatrienes, characterized in that an organometallic 1-heptenyl compound is reacted with a (E)-1,3-butadiene derivative.

Manufacture of 1,3,5-undecatrienes that can be used in the perfumes and flavorings industry.

8 Claims, No Drawings

NEW PROCESS FOR THE PREPARATION OF 1,3,5-UNDECATRIENES

The present invention relates to a new process for the synthesis of 1,3,5-undecatriene and, more precisely, of the 3E,5Z (I) and 3E,5E (II) isomers of this polyolefin.

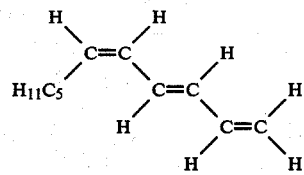

(3E,5Z)—1,3,5-undecatriene (I)

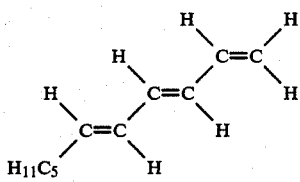

(3E,5E)—1,3,5-undecatriene (II)

These compounds were isolated from certain essential oils and were used for their flavouring and fragrant properties.

The industrial preparation of these isomers in the required stereochemistry presents numerous problems which have not yet been solved satisfactorily.

The first synthesis which was proposed (Recherches 16, 5–38, 1967) necessitates numerous stages with yields that are incompatible with industrial requirements.

On the other hand, application of the processes of French Patent Application No. 2.309.498 necessitates either the lengthy and delicate preparation of a pentadienyltriphenylphosphonium halide, or the use of 1-butene-3,4-epoxide, the carcinogenic properties of which are known in another connection.

The more recent methods do not have any advantage since they necessitate either the difficult preparation of a particularly unstable sulphone (Tetrahedron Letters 23 (48), 5053–5046, 1982), or the semireduction of a conjugated triple bond, an operation which is difficult to carry out on an industrial scale (Tetrahedron Letters 24 (5), 489–492, 1983), or the preparation of an unstable lithium derivative at a very low temperature (Tetrahedron Letters 24 (6), 2665–2668, 1983), or the decyclisation of polycyclic perhydrothiophenes at a very high temperature (Tetrahedron Letters 26 (10), 1301–1304, 1985).

The applicant has now discovered a new process for the preparation of (3E,5Z)-1,3,5-undecatriene and its 3E,5E isomer, which process is highly stereoselective and particularly simple and advantageous compared with the known processes.

The invention relates more precisely to a process for the preparation of (3E,5Z)-1,3,5-undecatriene in the pure state (or in admixture with (3E,5E)-1,3,5-undecatriene), characterised in that an organometallic (Z)-1-heptenyl compound in the pure state (or in admixture with the organometallic compound corresponding to the 1E isomer) of the formula:

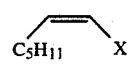

(III)

in which the symbol X represents a leaving group chosen from transition metals or magnesium halides, is reacted, at room temperature or at a slightly lower or higher temperature, with a (E)-1,3-butadiene derivative of the formula:

$$Y\diagdown\diagup\diagdown\diagup \qquad (IV)$$

in which the symbol Y represents a leaving group chosen from halogen atoms or alkylthio radicals (having from 1 to 4 carbon atoms), in the presence of a metal catalyst and in an inert organic solvent, and the reaction medium is then hydrolysed with a saturated aqueous salt solution.

At present, those derivatives of the formula III in which X represents copper, or magnesium chloride or bromide are preferred.

According to the process of the invention, the reaction of the compounds of the general formula III with the compounds of the general formula IV is carried out in the presence of an inert organic solvent, preferably an ether.

The reaction temperature depends on several factors, especially on the duration of the reaction, on the nature of the catalysts and on the solvent used. In general, the said reaction is carried out at a temperature of from $-20°$ C. to $+60°$ C.; such limiting values should not, however, be regarded as absolute.

The catalyst used is an organometallic complex of a transition metal, more precisely nickel or palladium.

The above-described process, which is the subject of the present invention, permits (3E,5Z)-1,3,5-undecatriene (I), or mixtures of I and II, to be obtained in good yields and with a limited number of reaction stages.

The novelty of the invention lies in the particular choice of simple starting products which make possible a particularly advantageous process. Furthermore, the reaction of a vinyl organomagnesium compound with a dienic sulphide is surprising, since these two products are inert in the absence of a transition metal.

The present invention is illustrated in more detail by means of the Examples below:

EXAMPLE 1

(3E,5Z)-1,3,5-undecatriene (I) and (3E,5E)-1,3,5-undecatriene (II)

50:50 mixture 100 millimoles of magnesium 1-heptenyl bromide (mixture of two isomers Z and E in a ratio by weight of 50% and 50%) are added to a solution of 50 millimoles of (E)-1,3-butadiene butyl sulphide and 3.25 millimoles of nickel (2+) bis(triphenylphosphine) bromide in 200 ml of tetrahydrofuran. The reaction is allowed to proceed, without the reaction medium being cooled, until the starting materials have disappeared completely. The mixture is then hydrolysed with 100 ml of a saturated ammonium chloride solution or another saturated aqueous salt solution. The mixture is stirred for one hour. It is then decanted and the organic phase is recovered. The reaction medium is then washed a second time with the saturated aqueous salt solution and the organic phase is recovered. The organic phase is dried over anhydrous magnesium sulphate and the solvent is removed by evaporation under reduced pressure (20 mmHg) and at a temperature of 30° C. A mixture of (3E,5Z)-1,3,5-undecatriene (I) and (3E,5E)-1,3,5-undecatriene (II) is obtained. This mixture is distilled in the presence of an antioxidant under reduced pressure (0.05 mmHg) and at a temperature of 35° C. in order to obtain a pure mixture of compounds of the formulae I and II.

The yield of the reaction is 50%.

The composition of the mixture was determined by gas phase chromatography with a WCOT WAX 57 CB capillary column 10 meters in length, the temperature being programmed at 90° C.-200° C., 4° C./min. A mixture of I and II is obtained in a ratio by weight of 1:1.

The magnesium 1-heptenyl halide used as the starting product can be synthesised from (E)-2,3 dibromooctanoic acid according to the method described by Norris (J. Org. Chem. (1959), 25, 1579). The synthesis of (E)-1,3-butadiene butyl sulphide is known (Everhardus et al. Rech. Trav. Chim. Pays-Bas 93, 90, 1974).

The two isomers I and II can be obtained in the pure state by separation of the mixture obtained previously by means of preparative gas phase chromatography (stationary phase 50% Carbowax).

The spectral characteristics of the two isomers are as follows:

A—Proton nuclear magnetic resonance spectra, recorded at 200 MHz in solution in deuterated chloroform.

$$H_3^{10}C=(CH_2^9)_3-CH_2^8-CH^7=CH^6-H^5C=CH^4-H^3C=C \diagup_{H^1}^{H_2}$$

| (3E,5Z)—1,3,5-undeca-triene (I) | (3E,5E)—1,3,5-undeca-triene (II) | Allocation |
|---|---|---|
| 0.88 (t) | 0.87 (t) | $3H^{10}$ |
| 1.30 (m) | 1.28 (m) | $6H^9$ |
| 2.18 (m) | 2.08 (m) | $2H^8$ |
| 5.06 | 5.05 | $1H^1$ |
| 5.19 | 5.18 | $1H^2$ |
| 5.47 | 5.74 | $1H^7$ |
| 6.02 | | $1H^6$ |
| 6.19 | 5.98–6.24 (m) | $1H^4$ |
| 6.39 | | $1H^3$ |
| 6.51 | | $1H^5$ |

B—Infra-red spectra, in solution in carbon tetrachloride.

(3E,5Z)-1,3,5-undecatriene (cm$^{-1}$): 3100, 3020, 1625, 1580, 900, 1000, 940, 750, 720.

(3E,5E)-1,3,5-undecatriene (cm$^{-1}$): 3100, 3030, 1630, 1585, 900, 1000, 975, 720.

C—Mass spectrum, recorded at 70 eV, on electron impact, after separation by chromatography:

(3E,5Z)-1,3,5-undecatriene (m/z): 150(M+26%), 107(2%), 93(22%), 91(30%), 80(72%), 79(100%), 77(41%), 67(14%), 53(5%), 41(25%).

(3E,5E)-1,3,5-undecatriene (m/z): 150(M+25%), 107(1%), 93(22%), 91(30%), 80(63%), 79(100%), 77(41%), 67(11%), 53(4%), 41(23%).

EXAMPLE 2

(3E,5Z)-1,3,5-undecatriene (I) and (3E,5E)-1,3,5-undecatriene (II).

70:30 mixture 100 millimoles of magnesium 1-heptenyl bromide (mixture of two isomers Z and E in a ration by weight of 70% and 30%) are added to a solution of 50 millimoles of (E)-1,3-butadiene ethyl sulphide and 3.25 millimoles of nickel (2+) bis(triphenylphosphine) bromide in 200 ml of tetrahydrofuran. The reaction is allowed to proceed, without cooling, for approximately 3 hours. The mixture is hydrolysed with 100 ml of a saturated ammonium chloride solution, while cooling in an ice bath. The mixture is stirred for one hour, decanted, and the organic phase is recovered. The reaction medium is washed a second time under the conditions described above.

After the two phases have been separated, the organic solution is dried over anhydrous magnesium sulphate and the solvent is removed under the conditions described in Example 1. A mixture of (3E,5Z)-1,3,5-undecatriene (I) and (3E,5E)-1,3,5-undecatriene (II) is obtained in a ratio by weight of 7:3.

The composition of the mixture was determined by gas phase chromatography under the conditions described in Example 1.

The overall yield of the reaction is approximately 48%.

EXAMPLE 3

(3E,5Z)-1,3,5-undecatriene (I) and (3E,5E)-1,3,5-undecatriene (II).

60:40 mixture 1.3 millimoles of nickel (2+) bis(triphenylphosphine) bromide and 100 millimoles of magnesium 1-heptenyl bromide (mixture of two isomers Z and E in a ratio by weight of 6:4), dissolved in tetrahydrofuran, are added, under nitrogen and while cooling, to a solution of 50 millimoles of (E)-1-chloro-1,3-butadiene in 200 ml of tetrahydrofuran. The mixture is heated at 35° C. for approximately 1 hour and the reaction medium is then hydrolysed with a saturated ammonium chloride solution. The mixture is decanted. The organic phase is washed twice with 25 ml of the saturated aqueous solution each time. The organic phase is dried over anhydrous magnesium sulphate. The solvent is removed by evaporation under reduced pressure (20 mmHg) and at a temperature of 30° C. A mixture of (3E,5Z)-1,3,5-undecatriene (I) and (3E,5E)-1,3,5-undecatriene (II) is obtained. The mixture is distilled under reduced pressure (0.02 mmHg) and at a temperature of 30° C. in order to obtain a pure mixture of two isomers in a ratio by weight of 6:4.

The overall yield of the reaction is 54%.

The composition of the mixture was confirmed by gas phase chromatography with a capillary column under the conditions described in Example 1.

The (E)-1-chloro-1,3-butadiene used as the starting product is synthesised according to the method described by Klebauskii (J. Gen. Chem. (1947), 17, 235).

EXAMPLE 4

(3E,5Z)-1,3,5-undecatriene (I)

1.8 millimoles of nickel (O) bis(triphenylphosphine) bromide, followed by 50 millimoles of (E)-1-chloro-1,3- butadiene dissolved in 50 ml of tetrahydrofuran, are added, while cooling, to a solution of 60 millimoles of (Z)-1-heptenyl copper in 100 ml of a mixture of tetrahydrofuran and diethyl ether (75:25). The reaction is allowed to proceed for 30 minutes, while stirring without cooling. The reaction medium is then hydrolysed with 70 ml of a saturated aqueous ammonium chloride solution. The mineral salts formed are removed and 100 ml of ethyl ether are added. The organic phase is washed once with the saturated aqueous ammonium chloride solution and is then dried over anhydrous magnesium sulphate. The organic solvents are evaporated and the residue is distilled under reduced pressure (0.01 mmHg) at a temperature of 26° C.

The spectral characteristics of the product thus obtained are identical with those described in Example 1 for (3E,5Z)-1,3,5-undecatriene (I) (91% purity).

The yield of the reaction is 65%.

The (Z)-1-heptenyl copper is synthesised according to the method of Alexakis (J. Organomet. Chem. (1979), 177, 293–298).

What is claimed is:

1. Process for the preparation of (3E,5Z)-1,3,5-undecatriene, characterised in that an organometallic (Z)-1-heptenyl compound of the formula:

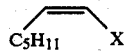

in which X represents a leaving group chosen from transition metals or magnesium halides, is reacted, at a temperature of from −20° C. to +60° C., with a (E)-1,3-butadiene derivative of the formula:

in which Y represents a leaving group chosen from halogen atoms or alkylthio radicals having from 1 to 4 carbon atoms, in the presence of a metal catalyst and in an organic solvent, and the reaction medium is hydrolyzed with a saturated aqueous salt solution.

2. Process according to claim 1, in which X represents a copper atom, or magnesium chloride or bromide.

3. Process according to claim 1, characterised in that the catalyst used is an organometallic complex of a transition metal.

4. Process according to claim 3, in which the transition metal is nickel or palladium.

5. Process according to claim 3 characterised in that the catalyst is nickel (2+) bis(triphenylphosphine) bromide or nickel (O) bis(triphenylphosphine) bromide.

6. Process according to claim 1, characterised in that the reaction is carried out at a temperature of from 0° C. to +40° C.

7. Process according to claim 4, characterised in that the catalyst is nickel (2+) bis(triphenylphosphine) bromide or nickel (O) bis(triphenylphosphine) bromide.

8. Process of claim 1 wherein the starting organometallic compound comprises the (E)-1-heptenyl isomer, and the product comprises (3E,5E)-1,3,5-undecatriene.

* * * * *